United States Patent
Nakagawa et al.

(10) Patent No.: US 10,551,252 B2
(45) Date of Patent: Feb. 4, 2020

(54) INTERNAL TEMPERATURE MEASURING APPARATUS AND SENSOR PACKAGE

(71) Applicant: OMRON Corporation, Kyoto-shi, Kyoto (JP)

(72) Inventors: Shinya Nakagawa, Omihachiman (JP); Masao Shimizu, Moriyama (JP)

(73) Assignee: OMRON Corporation, Kyoto-shi (JP)

( * ) Notice: Subject to any disclaimer, the term of this patent is extended or adjusted under 35 U.S.C. 154(b) by 305 days.

(21) Appl. No.: 15/552,619

(22) PCT Filed: Feb. 25, 2016

(86) PCT No.: PCT/JP2016/055558
§ 371 (c)(1),
(2) Date: Aug. 22, 2017

(87) PCT Pub. No.: WO2016/143529
PCT Pub. Date: Sep. 15, 2016

(65) Prior Publication Data
US 2018/0024010 A1    Jan. 25, 2018

(30) Foreign Application Priority Data
Mar. 12, 2015 (JP) ................................. 2015-049446

(51) Int. Cl.
*G01K 17/00* (2006.01)
*G01K 1/18* (2006.01)
*G01K 7/42* (2006.01)

(52) U.S. Cl.
CPC ............... *G01K 1/18* (2013.01); *G01K 7/427* (2013.01); *B81B 2201/0278* (2013.01)

(58) Field of Classification Search
CPC .......... H01L 35/00; H01L 35/32; G01K 7/00; G01K 13/00; G01K 7/06; G01K 7/02; G01K 7/028; G01K 17/00; G01K 7/226
(Continued)

(56) References Cited

U.S. PATENT DOCUMENTS 2,017,021 A * 10/1935 Tepper ...................... B68B 1/06
54/7
7,875,791 B2 * 1/2011 Leonov ..................... G01J 5/12
136/203
(Continued)

FOREIGN PATENT DOCUMENTS

CN  101946166 A  1/2011
CN  103185611 A  7/2013
(Continued)

OTHER PUBLICATIONS

Chinese office action letter dated Dec. 5, 2018 in a counterpart Chinese patent application.
(Continued)

*Primary Examiner* — Gail Kaplan Verbitsky
(74) *Attorney, Agent, or Firm* — Metrolex IP Law Group, PLLC

(57) ABSTRACT

An internal temperature measuring apparatus includes: a sensor package in which a MEMS chip and a temperature sensor are disposed in a bottomed tubular package, the MEMS chip including one or a plurality of thermopiles each of which measures a heat flux passing through a region of a bottom of the bottomed tubular package, the temperature sensor measuring a reference temperature used as temperature of a predetermined portion of the MEMS chip; and a printed circuit board configured to calculate the internal temperature of the measurement object based on output of the sensor package. An outer bottom face of the sensor package projects from a plate face of the printed circuit board through a through-hole made in the printed circuit board.

8 Claims, 4 Drawing Sheets

(58) Field of Classification Search
USPC .......... 374/29, 30, 179, 170, 141, 135, 208
See application file for complete search history.

(56) References Cited

U.S. PATENT DOCUMENTS

| | | | |
|---|---|---|---|
| 9,117,949 B2* | 8/2015 | Mao | G01J 5/022 |
| 9,513,240 B2* | 12/2016 | Lin | G01N 25/4893 |
| 9,976,914 B2* | 5/2018 | Radhakrishnan | G01K 7/02 |
| 10,018,510 B2* | 7/2018 | Schilz | G08B 13/193 |
| 10,139,256 B2* | 11/2018 | Zhao | G01F 1/6845 |
| 10,190,921 B2* | 1/2019 | Nakagawa | A61B 5/01 |
| 10,295,490 B2* | 5/2019 | Jia | G01K 17/006 |
| 2004/0113076 A1* | 6/2004 | Guo | G01H 11/08 |
| | | | 250/338.1 |
| 2004/0187904 A1* | 9/2004 | Krellner | G01J 5/10 |
| | | | 136/213 |
| 2008/0262773 A1 | 10/2008 | Howell | |
| 2009/0206264 A1* | 8/2009 | Twiney | G01J 5/041 |
| | | | 250/353 |
| 2015/0010040 A1 | 1/2015 | Ito et al. | |
| 2017/0038235 A1* | 2/2017 | Zhao | G01F 1/6845 |
| 2017/0038237 A1* | 2/2017 | Chen | E21B 43/34 |
| 2017/0147879 A1* | 5/2017 | Alameh | G06F 1/1684 |
| 2017/0307553 A1* | 10/2017 | Jia | G01K 17/006 |
| 2018/0072563 A1* | 3/2018 | Huang | B81B 7/0067 |
| 2018/0106681 A1* | 4/2018 | Buydens | G01J 5/0003 |
| 2019/0148424 A1* | 5/2019 | Kropelnicki | G01J 5/048 |
| | | | 257/293 |

FOREIGN PATENT DOCUMENTS

| | | |
|---|---|---|
| CN | 104051370 A | 9/2014 |
| JP | 2002-372464 A | 12/2002 |
| JP | 2007-212407 A | 8/2007 |
| WO | 2013/141153 A1 | 9/2013 |

OTHER PUBLICATIONS

International Search Report of PCT/JP2016/055558 dated Mar. 22, 2016.

English translation of Written Opinion of PCT/JP2016/055558 dated Mar. 22, 2016 from the International Searching Authority.

* cited by examiner

INTERNAL TEMPERATURE MEASURING APPARATUS AND SENSOR PACKAGE

TECHNICAL FIELD

The present invention relates to an internal temperature measuring apparatus and a sensor package.

BACKGROUND ART

Conventionally, methods in which a sensor module having a configuration in FIG. 6A is used (for example, see PTL 1) and a method in which a sensor module having a configuration in FIG. 6B is used (for example, see PTL 2) are known as a method for detecting a heat flow flowing out from a body surface and measuring (calculating) a core body temperature from a detection result.

For use of one sensor module in FIG. 6A, namely, a heat flux sensor in which a temperature sensor is attached to each of top and bottom surfaces of a heat insulator, a core body temperature Tb is calculated using the following equation (1) from a temperature Ta measured with the temperature sensor on the top side of the heat insulator and a temperature Tt measured with the temperature sensor on the bottom side of the heat insulator.

$$Tb = (Tt-Ta)Rx/R1 + Tt \quad (1)$$

Where R1 and Rx are a heat resistance of a heat insulator and a heat resistance of a subcutaneous tissue, respectively.

In the internal temperature calculating method in which the sensor module in FIG. 6A is used, basically fixed values are used as the heat resistances R1 and Rx. However, because the heat resistance Rx depends on a location or an individual, a measurement error is included in the core body temperature Tb, which is calculated from the equation (1) using the fixed value as the heat resistance Rx, according to a difference between the heat resistance Rx used and the actual heat resistance Rx. Therefore, sometimes time changes of the temperatures Tt and Ta are measured, and the heat resistance Rx is calculated from the measurement result (see PTL 1).

In the case that an internal temperature is calculated with the sensor module in FIG. 6B, a temperature difference expressing a heat flux from the body surface is measured with each of two heat flux sensors having different heat resistances of the heat insulators. The following two equations can be obtained when the temperature difference is measured with the two heat flux sensors having different heat resistances of the heat insulators.

$$Tb = (Tt-Ta)Rx/R1 + Tt \quad (2)$$

$$Tb = (Tt'-Ta')Rx/R2 + Tt' \quad (3)$$

Where Ta and Ta' are temperatures measured with the temperature sensors on the top sides of the right and left heat flux sensors in FIG. 6B. Where Tt and Tt' are temperatures measured with the temperature sensors on the bottom sides of the right and left heat flux sensors in FIG. 6B. R1 and R2 are heat resistances of heat insulators of the heat flux sensors as illustrated in FIG. 6B.

In the case that R1 and R2 are known numbers, only Rx and Tb are unknown numbers in the equation (2). Accordingly, the core body temperature Tb can be obtained from the equations (2) and (3). In the case that the internal temperature is calculated using the sensor module in FIG. 6B, the core body temperature Tb is measured (calculated) by the principle.

PRIOR ART DOCUMENTS

Patent Documents

Patent Document 1: Japanese Unexamined Patent Publication No. 2002-372464
Patent Document 2: Japanese Unexamined Patent Publication No. 2007-212407

SUMMARY OF THE INVENTION

Problems to be Solved by the Invention

In the sensor modules in FIGS. 6A and 6B, information necessary for the calculation of the core body temperature Tb is obtained with plural temperature sensors. Because the temperature sensor does not have so high accuracy, the heat insulator having the high heat resistance and heat capacity is used in the sensor modules of FIGS. 6A and 6B. Therefore, the sensor modules have poor responsiveness (it takes a long time to obtain a stable measurement result of the core body temperature).

When a MEMS chip including a thermopile is used in the measurement of the temperature difference, the core body temperature can be measured with good responsiveness because of large decreases in heat resistance and heat capacity of the sensor module that measures the core body temperature. Therefore, an internal temperature measuring apparatus in which the MEMS chip is used is being developed. However, the MEMS chip and the measurement object are hardly brought into thermally good contact with each other in a configuration of the existing internal temperature measuring apparatus in which the MEMS chip is disposed on the printed wiring board.

An object of the present invention is to provide an internal temperature measuring apparatus in which the MEMS chip and the measurement object are brought into thermally good contact with each other and a sensor package used to produce the internal temperature measuring apparatus.

Means for Solving the Problem

According to one aspect of the present invention, an internal temperature measuring apparatus that measures an internal temperature of a measurement object, the internal temperature measuring apparatus includes: a sensor package in which a MEMS chip and a temperature sensor are disposed in a bottomed tubular package, the MEMS chip comprising one or plural thermopiles each of which measures a heat flux passing through a region of a bottom of the bottomed tubular package, the temperature sensor measuring a reference temperature used as temperature of a predetermined portion of the MEMS chip; and a printed circuit board configured to calculate the internal temperature of the measurement object based on output of the sensor package. An outer bottom face of the sensor package projects from a plate face of the printed circuit board through a through-hole made in the printed circuit board.

That is, the internal temperature measuring apparatus has the configuration in which the MEMS chip is disposed on not the printed circuit board (a printed wiring board constituting the printed circuit board) but the bottom of the bottomed tubular package, and the configuration in which the outer bottom face of the bottomed tubular package projects from the plate face (bottom surface) of the printed circuit board. Accordingly, in the internal temperature measuring apparatus, the MEMS chip and the measurement object (such as the human body) can be brought into thermally good contact with each other.

At this point, the bottomed tubular package in the internal temperature measuring apparatus may be a package having shapes such as a bottomed cylindrical shape, a bottomed elliptical tube shape, and a bottomed rectangular tube shape, and including a bottom and a sidewall surrounding the bottom. In the internal temperature measuring apparatus, the bottom of the bottomed tubular package may include a non-heat transfer portion and a heat transfer portion made of a material (for example, metal) having heat conductivity better than that of a constituent material of the non-heat transfer portion, and at least a part of the MEMS chip may be located on the heat transfer portion.

In the internal temperature measuring apparatus, the bottomed tubular package of the sensor package may include plural leads, in which surfaces oriented toward an identical direction at leading ends on an outside of a tubular wall of the bottomed tubular package are located on an identical plane, piercing the tubular wall, and the sensor package may be mounted on the printed circuit board using the surfaces at the leading ends of the plural leads. When the above configuration is adopted in the internal temperature measuring apparatus, the internal temperature measuring apparatus can easily be produced (assembled) compared with adoption of another configuration. In order to improve thermal contact performance between the MEMS chip and the measurement object (such as a human body), the outer bottom face of the sensor package may have a curved shape in which a central portion projects.

In the internal temperature measuring apparatus, the bottomed tubular package of the sensor package may be formed by mold forming. Therefore, the sensor package is easy to produce, so that the internal temperature measuring apparatus can easily be constructed (with a smaller total number of processes).

In the internal temperature measuring apparatus, in order that light incident from above is prevented from being incident on the MEMS chip after reflection by an inner surface of the sensor package, or in order to stabilize temperature of air in the sensor package 10, an inner surface of the tubular wall of the bottomed tubular package may be coated with a black material.

According to another aspect of the present invention, a sensor package that obtains data used to calculate an internal temperature of a measurement object, the sensor package includes: a bottomed tubular package; a MEMS chip disposed in the bottomed tubular package, the MEMS chip comprising one or plural thermopiles each of which measures a heat flux passing through a region of a bottom of the bottomed tubular package; and a temperature sensor disposed in the bottomed tubular package, the temperature sensor measuring a reference temperature used as temperature of a predetermined portion of the MEMS chip. The bottomed tubular package comprises plural leads, in which surfaces oriented toward an identical direction at leading ends on an outside of a tubular wall of the bottomed tubular package are located on an identical plane, piercing the tubular wall.

Accordingly, the use of the sensor package of the present invention can construct the internal temperature measuring apparatus in which the MEMS chip and the measurement object are brought into thermally good contact with each other.

Effect of the Invention

The present invention can provide the internal temperature measuring apparatus in which the MEMS chip and the measurement object are brought into thermally good contact with each other.

MODE FOR CARRYING OUT THE INVENTION

Hereinafter, an embodiment of the present invention will be described with reference to the drawings.

Figure 1:
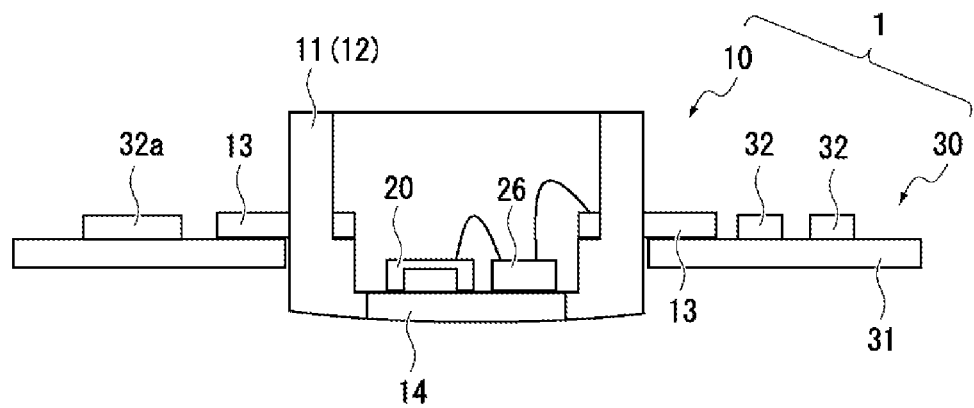
FIG. 1 is a schematic configuration diagram illustrating an internal temperature measuring apparatus according to an embodiment of the present invention.

FIG. 1 illustrates a schematic configuration of an internal temperature measuring apparatus 1 according to an embodiment of the present invention.

The internal temperature measuring apparatus 1 is developed as a device that measures an internal temperature (core body temperature) of a human body. As illustrated in FIG. 1, the internal temperature measuring apparatus 1 includes a sensor package 10 and a printed circuit board 30.

The printed circuit board 30 is a unit in which various devices 32 (such as a resistor and a capacitor) including an arithmetic circuit 32a are mounted on a printed wiring board 31. The arithmetic circuit 32a calculates the internal temperature of a measurement object from measurement results of a temperature difference and a temperature with the sensor package 10 (a MEMS chip 20 and an ASIC 26 (to be described later)), and outputs the internal temperature.

As illustrated in FIG. 1, a through-hole is made in the printed wiring board 31 of the printed circuit board 30 to insert the sensor package 10. In the sensor package 10, plural lands (not illustrated) are provided around the through-hole such that each land is opposite to the lead 13 inserted in the through-hole.

The sensor package 10 is a module that measures a value (a temperature and at least one temperature difference) necessary for the calculation of the internal temperature. The internal temperature measuring apparatus 1 is used while a bottom face of the sensor package 10 in FIG. 1 is brought into contact with a surface of a human body. Hereinafter, in the sensor package 10 and the internal temperature measuring apparatus 1, the top and bottom in FIG. 1 are simply referred to as a top and a bottom.

The sensor package 10 is a module in which the MEMS chip 20 and the ASIC 26 are disposed in an inner bottom face of a package 11. As illustrated in FIG. 1, the package 11 in which a bottom face is formed into a curved shape having a downwardly-projected central portion, is used in the sensor package 10 so as to be brought into thermally good contact with the surface of the human body.

The package 11 will more specifically be described below.

Figure 2:
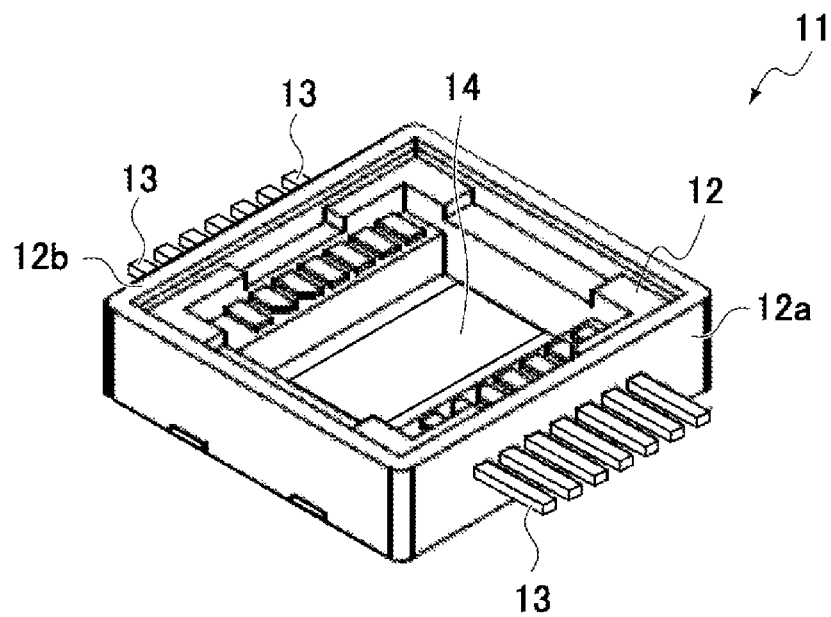
FIG. 2 is a perspective view illustrating a package used in a sensor package of the internal temperature measuring apparatus of the embodiment.

FIG. 2 illustrates a configuration of the package 11. As illustrated in FIG. 2, the package 11 includes a casing 12 having a substantially bottomed square tube shape. In the package 11, plural leads 13 are provided in each of sidewalls 12a and 12b opposite to each other while piercing portions at a predetermined level from the inner bottom face of the casing 12. A position where the lead 13 pierces each of the sidewall 12a and 12b is fixed such that the bottom surface of the sensor package 10 projects from the bottom surface of the printed circuit board 30 (printed wiring board 31) when the bottom side of the sensor package 10 is inserted in the through-hole of the printed wiring board 31.

A bottom of the casing 12 of the package 11 is constructed with a heat transfer pad 14 made of a high heat conductive material (in the embodiment, metal) and a portion made of a low heat conductive material. The heat transfer pad 14 is provided in order to favorably transfer heat from a human body to the MEMS chip 20 and the ASIC 26, and a shape of the heat transfer pad 14 is fixed such that the MEMS chip 20 and the ASIC 26 can be disposed on the heat transfer pad 14.

Any material having relatively poor heat conductivity may be used as a constituent material of the sidewall of the casing 12, and a material having heat conductivity poorer than that of the heat transfer pad 14 may be used as a constituent material except for the heat transfer pad 14 in the bottom of the casing 12 (hereinafter, also referred to as a casing bottom). However, when the constituent material of the sidewall of the casing 12 and the constituent material except for the heat transfer pad 14 in the casing bottom are made of the same resin, the package 11 can be produced by mold forming (insert forming). Accordingly, the constituent material of the sidewall of the casing 12 and the constituent material except for the heat transfer pad 14 in the casing bottom are preferably made of the same resin.

The MEMS chip 20 (FIG. 1) is a compact temperature difference sensor (heat flux sensor), which is produced using a MEMS technology so as to include at least one thermopile that measures the temperature difference generated in the MEMS chip 20 by the in-flow heat flux through the casing bottom of the package 11.

A specific configuration of the MEMS chip 20 used in the sensor package 10 depends on the calculation method adopted to calculate the internal temperature. As described in "BACKGROUND ART", the method for calculating the internal temperature includes the method in which the two temperature differences (Tt−Ta and Tt'−Ta') are required and the method in which only one temperature difference is required.

The MEMS chip 20 including at least one thermopile that measures ΔT (the temperature difference corresponding to "Tt−Ta") and at least one thermopile that measures ΔT' (the temperature difference corresponding to "Tt'−Ta'") is used in the case that the former method is adopted to calculate the internal temperature. The MEMS chip 20 including at least one thermopile that measures ΔT (one kind of the temperature difference) is used in the case that the latter method is adopted to calculate the internal temperature.

Figure 3A:
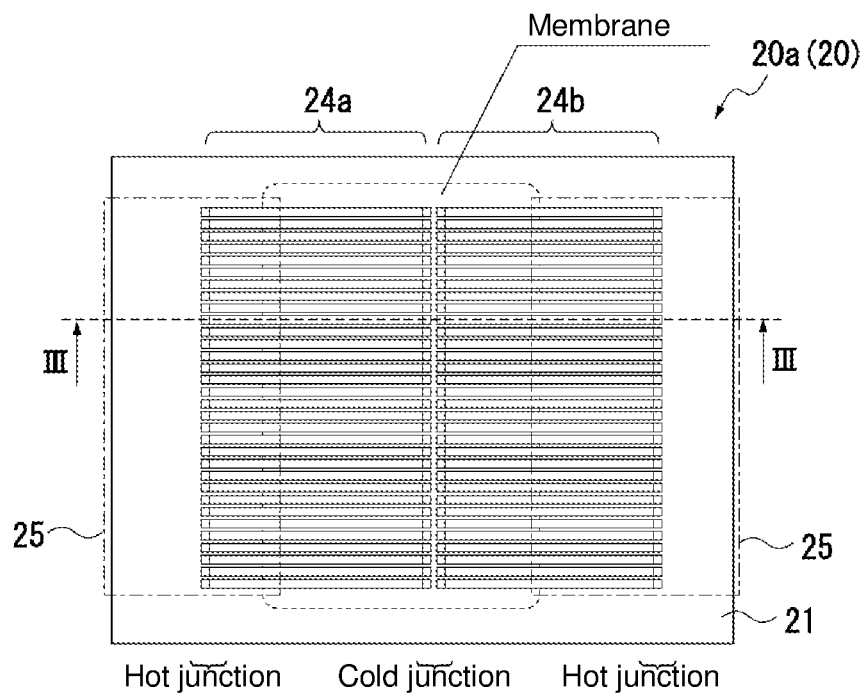
FIG. 3A is a top view illustrating a MEMS chip disposed in the package.
Figure 3B:
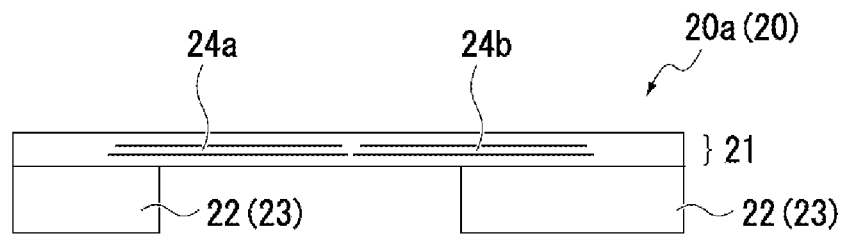
FIG. 3B is a sectional view taken on line III-III of the MEMS chip in FIG. 3A.

A MEMS chip 20a that is an example of the MEMS chip 20 will be described below with reference to FIGS. 3A and 3B. FIG. 3A is a top view of the MEMS chip 20a, and FIG. 3B is a sectional view taken on line III-III of the MEMS chip 20a in FIG. 3A. Hereinafter, in the description of the MEMS chip 20, the top, the bottom, the right, and the left mean the top, the bottom, the right, and the left in FIG. 3B.

As illustrated in FIG. 3B, the MEMS chip 20a includes a top face 21 and a support 22. The top face 21 is formed on a silicon substrate using various semiconductor processes (such as film forming, resist pattern forming, and etching). The support 22 is formed by etching of the silicon substrate on which the top face 21 is formed from a backside (the lower side in FIG. 3B).

As illustrated in FIG. 3B, the support 22 of the MEMS chip 20a includes at least one cavity (etched portion) leading to the top face 21. Hereinafter, in the top face 21, a portion located above the cavity of the support 22 is referred to as a membrane. In the support 22, a portion (in the top face 21, a portion of the support 22 located below the portion that becomes a temperature measurement target with a thermopile 24) in a frame 25 indicated by an alternate long and short dash line in FIG. 3A is referred to as a leg 23.

As illustrated in FIGS. 3A and 3B, thermopiles 24a and 24b in each of which plural thermocouples are connected in series are provided in the top face 21 of the MEMS chip 20a. Although not illustrated, an electrode is provided in an upper surface of the top face 21 of the MEMS chip 20a in order to take out output of the thermopile 24.

Each thermocouple constituting the thermopile 24a is substantially equal to each thermocouple constituting the thermopile 24b in a length. As illustrated in FIG. 3A, the hot junction and the cold junction of each thermocouple constituting the thermopile 24a are disposed on the leg 23 on the left of the MEMS chip 20a (in the support 22, the portion in the left frame 25 indicated by the alternate long and short dash line) and in a substantial center of a horizontal direction of the MEMS chip 20a in the membrane, respectively. The hot junction and the cold junction of each thermocouple constituting the thermopile 24b are disposed on the leg 23 on the right of the MEMS chip 20a and in the substantial center of the horizontal direction of the MEMS chip 20a in the membrane, respectively.

The center in the horizontal direction of the cavity included in the support 22 of the MEMS chip 20a is located on the left of the center in the horizontal direction of the MEMS chip 20a. Resultantly, in the MEMS chip 20a, a heat resistance of a heat path from the bottom surface of the left leg 23 to the portion in which the cold junction group of the thermopile 24a is provided in the top face 21 is larger than a heat resistance of a heat path from the bottom surface of the right leg 23 to the portion in which the cold junction group of the thermopile 24b is provided in the top face 21.

Therefore, the MEMS chip 20a acts as a device in which thermopile 24a measures the temperature difference ΔT while the thermopile 24b measures the temperature difference ΔT' (<ΔT).

The ASIC 26 (FIG. 1) is an integrated circuit in which plural input and output electrodes are provided on the top surface of the integrated circuit. The ASIC 26 includes a temperature sensor. The ASIC 26 has a function of amplifying output of the temperature sensor and output of each thermopile 24 of the MEMS chip 20 and a function of digitizing each amplified output. For example, an integrated circuit including a proportional to absolute temperature (PTAT) voltage source that outputs voltage proportional to an absolute temperature (that is, a voltage source acting as a thermometer) can be used as the ASIC 26, a component of the PTAT voltage source acting as a temperature sensor.

As illustrated in FIG. 1, in the sensor package 10, the ASIC 26 and the MEMS chip 20 are disposed on the heat transfer pad 14 of the package 11 (casing 12), the MEMS chip 20 is electrically connected to the ASIC 26 by wire bonding, and the lead 13 is electrically connected to the ASIC 26 by wire bonding.

In the internal temperature measuring apparatus 1, the sensor package 10 is fixed to the printed circuit board 30 using the lead 13 while the bottom of the sensor package 10 having the above configuration is inserted in the through-hole of the printed circuit board 30 (printed wiring board 31).

Thus, the internal temperature measuring apparatus 1 has the configuration in which the MEMS chip 20 is disposed on not the printed circuit board 30 (the printed wiring board 31 that is of the component of the printed circuit board 30) but the inner bottom face of the package 11, and the configuration in which the bottom surface of the package 11 (an outer lower face of the package 11) projects from a plate face (bottom surface) of the printed circuit board 30. Additionally, the bottom surface of the sensor package 10 (package 11) of the internal temperature measuring apparatus 1 has the curved shape in which the central portion projects downward (toward the human body side). Accordingly, in the internal temperature measuring apparatus 1, the MEMS chip 20 and the human body can be brought into thermally good contact with each other.

Some descriptions about the internal temperature measuring apparatus 1 will be supplemented below.

Usually the MEMS chip 20 is fixed onto the heat transfer pad 14 using a good heat conductive adhesive such as a silver paste. At this point, the whole bottom surface of the MEMS chip 20 may be fixed onto the heat transfer pad 14 using the silver paste or the like. However, in such cases, because the cavity below the membrane becomes a closed space, a pressure of air in the cavity is increased by temperature rise, and possibly the membrane is broken.

Preferably the MEMS chip 20 is fixed onto the heat transfer pad 14 such that each cavity does not become the closed space. However, when the poor heat conductive portion exists between the leg 23 and the heat transfer pad 14, an error may be included in the temperature difference measured with the thermopile 24 in which the hot junction exists on the leg 23. When the MEMS chip 20 is fixed onto the heat transfer pad 14 while the silver paste is applied only to the whole bottom surface of each leg 23 of the MEMS chip 20, the occurrence of the breakage of the membrane due to the pressure increase of air in the cavity can be suppressed without degrading performance of the MEMS chip 20.

Accordingly, in producing (assembling) the sensor package 10, preferably the silver paste is applied only to the whole bottom surface of each leg 23 of the MEMS chip 20, and the MEMS chip 20 is fixed onto the heat transfer pad 14. However, some of the legs 23 that poorly conduct heat to the heat transfer pad 14 may exist depending on the configuration of the MEMS chip 20.

In the case that the MEMS chip 20 having the above configuration is used in the sensor package 10, MEMS chip 20 may be fixed onto the heat transfer pad 14 while the silver paste is applied only to the whole bottom surface of each leg 23 that is desirable to have the good heat conductivity to the heat transfer pad 14.

In the casing bottom (the bottom of the casing 12), the reason the heat transfer pad 14 having the high heat conductivity (see FIG. 1) is used as the portion where the MEMS chip 20 and the ASIC 26 are disposed is that in principle the temperature difference can correctly be measured for the good heat conductivity in a thickness direction of the casing bottom. However, in the case that the internal temperature is calculated from the temperature differences $\Delta T$ and $\Delta T'$, sometimes an estimated error (a difference between the calculation result of the internal temperature and the actual internal temperature) of the internal temperature increases because of the good heat conductivity in a crosswise direction (a direction perpendicular to the thickness direction) of the heat transfer pad 14. Accordingly, the casing bottom may be made of a material having relatively poor heat conductivity without providing the heat transfer pad 14 in the casing bottom.

In the temperature difference measuring apparatus in which MEMS chip 20 (for example, the MEMS chip 20a in FIGS. 3A and 3B) including the thermopile 24 for measuring the temperature difference $\Delta T$ and the thermopile 24 for measuring the temperature difference $\Delta T'$ is used, in order to prevent the estimated error of the internal temperature to increase due to the heat conduction in the crosswise direction of the casing bottom, the casing bottom may be configured such that heat transfer pads 14 are respectively provided under the leg 23 on the hot junction side of the thermopile 24 for measuring the temperature difference $\Delta T$ of the MEMS chip 20 and the leg 23 on the hot junction side of the thermopile 24 for measuring the temperature difference $\Delta T'$, and a poor heat conductive member is interposed between the heat transfer pads 14 to isolate the heat transfer pads 14 from each other.

Figure 4:
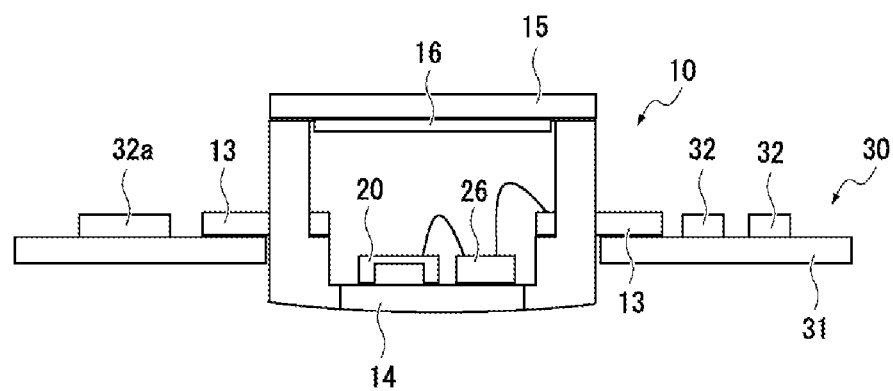
FIG. 4 is an explanatory diagram illustrating a use example of the internal temperature measuring apparatus of the embodiment.

In the case that a measurement environment is one in which the temperature of the air above the sensor package 10 is stable while light (such as infrared light) is not incident on the sensor package 10 from above, the sensor package 10 can be used in the state of FIG. 1, namely, the state in which the top of the sensor package 10 is not sealed. However, such a measurement environment occurs rarely. The measurement accuracy of the temperature difference is degraded in the case that the light is incident on the sensor package 10 from above, or in the case that the temperature of the air above the sensor package 10 changes. Therefore, as schematically illustrated in FIG. 4, the sensor package 10 is usually used while an opening (top surface) of the sensor package 10 is covered with a lid 15 larger than the opening.

The sensor package 10 is a module in which sensitivity becomes higher with decreasing air temperature above the sensor package 10. Accordingly, as illustrated in FIG. 4, a member 16 absorbing infrared light may be provided on the lower surface of the lid 15 in the case that the opening of the sensor package 10 is covered with the lid 15. A member formed into a shape having good heat dissipation, for example, a member including a radiation fin, or a member having an area several times larger than the size of the opening of the sensor package 10 may be used as the lid 15 of the sensor package 10.

Figure 5:
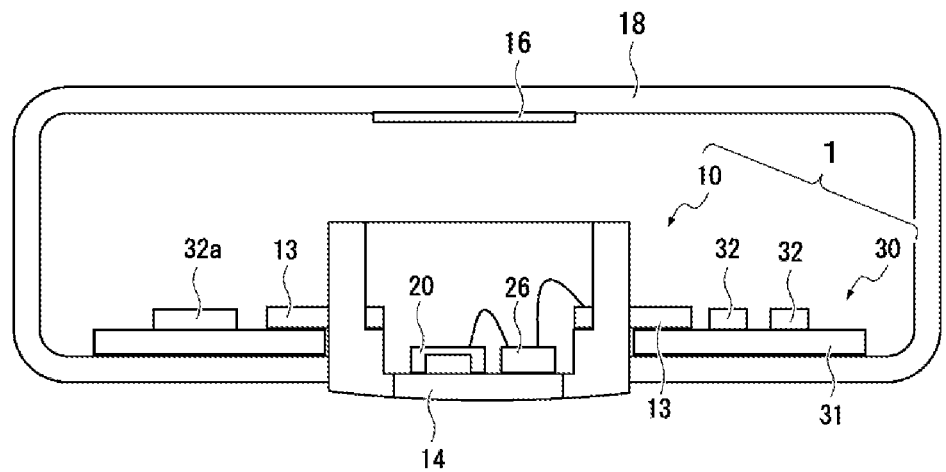
FIG. 5 is an explanatory diagram illustrating a use example of the internal temperature measuring apparatus of the embodiment.
Figure 6A:
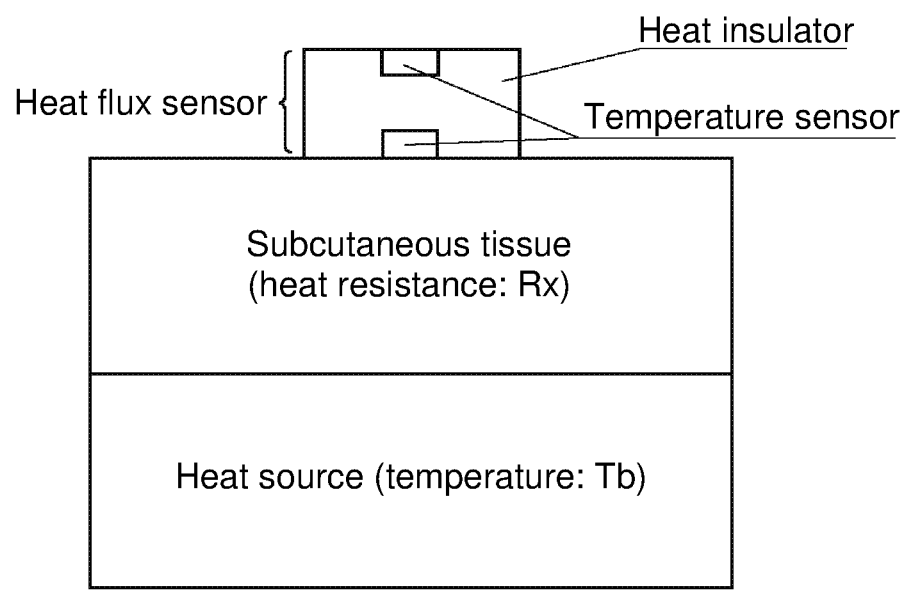
FIG. 6A is an explanatory diagram illustrating a sensor module used to measure (calculate) a core body temperature.
Figure 6B:
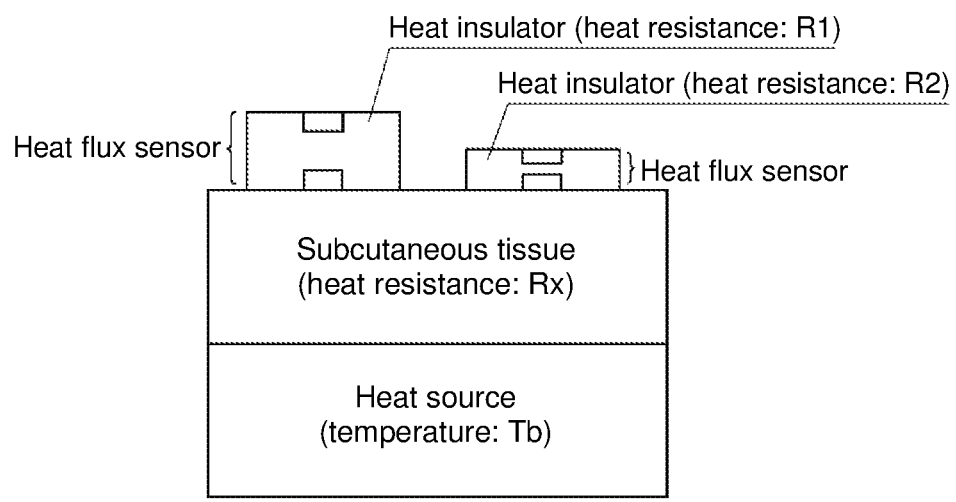
FIG. 6B is an explanatory diagram illustrating a sensor module used to measure (calculate) the core body temperature.

As schematically illustrated in FIG. 5, a portion except for the bottom surface of the sensor package 10 may be surrounded by a casing 18 without providing the lid 15.

In this case, in the casing 18, a member 16 absorbing infrared light is provided in the portion above the opening of the sensor package 10, which allows improvement of the sensitivity of the internal temperature measuring apparatus.

In order that the light incident from above is prevented from being incident on the MEMS chip 20 after reflection by an inner surface of the sensor package 10, or in order to stabilize the temperature of the air in the sensor package 10, the inner surface of the sensor package 10 (the package 11 and the casing 12) may be coated with a black material such as a black paint and a black resin.

An insulating film having biocompatibility or a resin member may be fixed to the bottom surface of the sensor package 10. Plural convex curved structures may be provided in the bottom surface of the sensor package 10 instead of forming the bottom surface of the sensor package 10 into the curved shape in which the central portion projects downwardly. The bottom surface of the sensor package 10 may be formed flat although thermal contact performance with the human body is slightly degraded.

In order to be able to mount the sensor package 10 on the printed circuit board 30 using the lead 13 (in order to be able to electrically and physically connect the sensor package 10 to the printed circuit board 30), surfaces oriented toward the same direction (a downward direction or an upward direction) at leading ends on the outsides of the plural leads 13 may be located on the same plane. Accordingly, the plural leads 13 of the sensor package 10 may be formed into a gull-wing shape. The package 11(casing 12) of the sensor package 10 may be formed into a shape (such as a bottomed rectangular tube shape, a bottomed cylindrical shape, and a bottomed elliptical tube shape, except for the bottomed square tube shape) different from the above shape, or the internal temperature measuring apparatus 1 may be modified into an apparatus that measures an internal temperature of a measurement object except for the human body.

DESCRIPTION OF SYMBOLS 1 internal temperature measuring apparatus
10 sensor package
11 package
12, 18 casing
12a, 12b sidewall
13 lead
14 heat transfer pad
15 lid
20 MEMS chip
21 top face
22 support
23 leg
24, 24a, 24b, 24c thermopile
26 ASIC
30 printed circuit board
31 printed wiring board
32 device
32a arithmetic circuit

The invention claimed is:

1. An internal temperature measuring apparatus that measures an internal temperature of a measurement object, the internal temperature measuring apparatus comprising:
   a sensor package in which a MEMS chip and a temperature sensor are disposed in a bottomed tubular package, the MEMS chip comprising one or a plurality of thermopiles each of which measures a heat flux passing through a region of a bottom of the bottomed tubular package, the temperature sensor measuring a reference temperature used as temperature of a predetermined portion of the MEMS chip; and
   a printed circuit board comprising an arithmetic circuit configured to calculate the internal temperature of the measurement object based on the heat flux measured by the one or the plurality of thermopiles and the reference temperature measured by the temperature sensor of the sensor package,
   wherein an outer bottom face of the sensor package projects from a plate face of the printed circuit board through a through-hole made in the printed circuit board.

2. The internal temperature measuring apparatus according to claim 1, wherein
   the bottom of the bottomed tubular package comprises:
      a non-heat transfer portion; and
      a heat transfer portion comprising a material having a heat conductivity higher than a heat conductivity of a constituent material of the non-heat transfer portion, and
   at least a part of the MEMS chip is located on the heat transfer portion.

3. The internal temperature measuring apparatus according to claim 2, wherein the heat transfer portion comprises a metal.

4. The internal temperature measuring apparatus according to claim 1, wherein the bottomed tubular package of the sensor package comprises a plurality of leads, in which surfaces oriented toward an identical direction at leading ends of the plurality of leads on an outside of a tubular wall of the bottomed tubular package are located on an identical plane, piercing the tubular wall, and
   the sensor package is mounted on the printed circuit board using the surfaces at the leading ends of the plurality of leads.

5. The internal temperature measuring apparatus according to claim 1, wherein the outer bottom face of the sensor package has a curved shape in which a central portion projects.

6. The internal temperature measuring apparatus according to claim 1, wherein the bottomed tubular package is formed by mold forming.

7. The internal temperature measuring apparatus according to claim 1, wherein an inner surface of a tubular wall of the bottomed tubular package is coated with a black material.

8. A sensor package that obtains data used to calculate an internal temperature of a measurement object, the sensor package comprising:
   a bottomed tubular package;
   a MEMS chip disposed in the bottomed tubular package, the MEMS chip comprising
      one or a plurality of thermopiles each of which measures a heat flux passing through a region of a bottom of the bottomed tubular package; and
      an arithmetic circuit configured to calculate the internal temperature of the measurement object; and
   a temperature sensor disposed in the bottomed tubular package, the temperature sensor measuring a reference temperature used as temperature of a predetermined portion of the MEMS chip,
   wherein
      the bottomed tubular package comprises a plurality of leads, in which surfaces oriented toward an identical direction at leading ends on an outside of a tubular wall of the bottomed tubular package are located on an identical plane, piercing the tubular wall, and
      the arithmetic circuit is configured to calculate the internal temperature of the measurement object using at least the measured heat flux and the measured reference temperature.

* * * * *